United States Patent [19]

Hirata et al.

[11] 4,362,736
[45] Dec. 7, 1982

[54] GUANIDINOTHIAZOLE COMPOUNDS, AND MEDICAL COMPOSITIONS CONTAINING THEM

[75] Inventors: Yasufumi Hirata, Omiya; Isao Yanagisawa, Tokyo; Yoshio Ishii, Omiya; Masaaki Takeda, Urawa, all of Japan

[73] Assignee: Yamanouchi Pharmaceutical Co., Ltd., Tokyo, Japan

[21] Appl. No.: 127,902

[22] Filed: Mar. 6, 1980

[30] Foreign Application Priority Data

Mar. 6, 1979 [JP] Japan .................................. 54-25745
Jun. 23, 1979 [JP] Japan .................................. 54-79508

[51] Int. Cl.³ ................. C07D 277/20; A61K 31/425
[52] U.S. Cl. .................................... 424/270; 548/193; 548/194; 548/195; 548/198
[58] Field of Search ............... 548/193, 194, 195, 148; 424/270

[56] References Cited

U.S. PATENT DOCUMENTS 4,165,378 8/1979 Gilmann et al. .................... 548/193
4,283,408 8/1981 Hirata et al. ........................ 424/270

Primary Examiner—Nicholas S. Rizzo
Attorney, Agent, or Firm—Burgess, Ryan and Wayne

[57] ABSTRACT

Novel guanidinothiazole compounds of the general formula

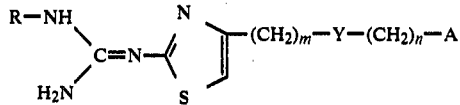

wherein R represents a hydrogen atom or a lower alkyl group, Y represents a sulfur atom or a methylene group, m and n each represents an integer of 1-3, A represents the group shown by

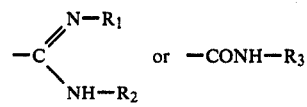

(wherein $R_1$ represents a hydrogen atom, a cyano group, a carbamoyl group, a ureido group, a hydroxyl group, a lower alkoxy group, a lower acyl group, an acylamino group, an arylsulfamoyl group, an aralkyl group or a carboxymethyl group, an arylsulfamoyl group, an aralkyl group or a carboxymethyl group, $R_2$ represents a hydrogen atom, a lower alkyl group, a lower alkenyl group, a lower alkynyl group, a cyano group or a lower acyl group, and $R_3$ represents a hydrogen atom, a lower alkyl group, a hydroxyl group or a sulfamoyl group), and the pharmacologically acceptable acid addition salts thereof; these compounds are useful as gastric acid secretion inhibitors.

9 Claims, No Drawings

GUANIDINOTHIAZOLE COMPOUNDS, AND MEDICAL COMPOSITIONS CONTAINING THEM

DETAILED EXPLANATION OF THE INVENTION

The present invention relates to novel guanidinothiazole compounds useful as gastric acid secretion inhibitors, the process for preparing them and the pharmaceutical compositions containing them.

Thus, according to this invention, there are provided novel guanidinothiazole compounds of the general formula

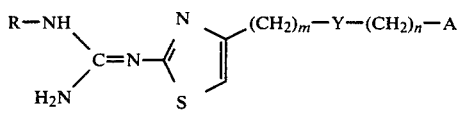

wherein R represents a hydrogen atom or a lower alkyl group, Y represents a sulfur atom or a methylene group, m and n each represents an integer of 1-3, A represents the group shown by

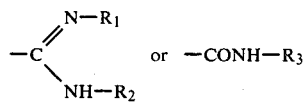 or —CONH—$R_3$ (wherein $R_1$ represents a hydrogen atom, a cyano group, a carbamoyl group, a ureido group, a hydroxyl group, a lower alkoxy group, a lower acyl group, an acylamino group, an arylsulfamoyl (—NH—$SO_2$—aryl) group, an aralkyl group or a carboxymethyl group, $R_2$ represents a hydrogen atom, a lower alkyl group, a lower alkenyl group, a lower alkynyl group, a cyano group or a lower acyl group, and $R_3$ represents a hydrogen atom, a lower alkyl group, a hydroxyl group or a sulfamoyl group), and the acid addition salts thereof capable of being supplied for pharmaceutical purposes.

Furthermore, according to other embodiments of this invention, there are provided a process for preparing the novel guanidinothiazole compounds of the general formula I and the medical compositions containing said guanidinothiazole compounds.

The term "lower" in the above definition means a straight or branched carbon chain having 1-5 carbon atoms. Therefore, as a lower alkyl group, there are a methyl group, an ethyl group, an isopropyl group, a butyl group, etc.; as a lower alkenyl group, there are a vinyl group, an allyl group, an isopropenyl group, etc.; as a lower alkynyl group, there are an ethynyl group, a propynyl group, a butynyl group, etc. Further, as an acylamino group, there are a lower acylamino group such as an acetylamino group, a propionylamino group, etc., and an arylcarbonylamino group such as a benzoylamino group, etc. Also, as an aralkyl group, there are a benzyl group, a phenethyl group, etc., and as a arylsulfamoyl group, there are a phenylsulfamoyl group, a naphthylsulfamoyl group, etc.

Furthermore, the compounds of the general formula I easily form acid addition salts thereof and there also exist the tautomers thereof at the position of

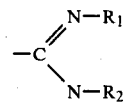

Therefore, the invention includes also the acid addition salts and the tautomers thereof.

As mentioned above, the guanidinothiazole compounds of this invention readily form acid addition salts capable of being used for medical purposes. As these salts, there are the salts of the guanidinothiazole compounds with inorganic acid or organic acids, for example, hydrochlorides, hydrobromides, sulfates, etc. Also, examples of the particularly useful organic acid salts are the salts with aliphatic carboxylic acids such as acetic acid, maleic acid, fumaric acid, etc.

It is the first feature of this invention that the compounds provided by this invention have a gastric acid secretion inhibitory activity and this activity is not caused by an anticholinergic activity. Since conventional commercially available gastric acid secretion inhibitors are mostly based on the anticholinergic activity and unwanted side effects caused by the anticholinergic activity have been pointed out, the compounds of this invention are useful as a new type gastric acid secretion inhibitors.

It is the second feature of this invention that the compounds of this invention have an activity for inhibiting gastric secretion through a histamine $H_2$-receptor. It has been proposed to classify histamine receptors into $H_1$-receptors and non $H_1$-receptors or $H_2$-receptors by Ash and Schild; "Brit. J. of Pharmacol. Chemother", 27, 427(1966) and Black et al.; "Nature", 236, 385 (1972). The effects of histamine on gastric acid secretion and heart rate in isolated guinea pig atrium are medicated by the $H_2$-receptor and these histamine effects are not inhibited by conventional antihistamines such as mepyramine but are antagonized by blockers of $H_2$-receptors such as metiamide.

Since a histamine $H_2$-receptor blocking agent has an activity for inhibiting the basic secretion of gastric acid and the gastric acid secretion induced by gastrin, histamine, methacholine or food, it can be used for the treatment of gastric ulcer and duodenal ulcer caused by the hypersecretion of gastric acid.

Hitherto, as the materials possessing the feature as in the compounds of this invention, the compounds in Belgian Pat. Nos. 804,145; 866,156; 867,105; 867,594 and U.S. Pat. No. 3,950,333, etc., are known but the compounds of this invention are all novel compounds having different structures and more superior pharmacological effects compared with those of the known compounds.

The compounds of this invention can be administered orally or parenterally but the oral administration is preferred. The compounds of this invention are used as the free bases or the pharmacologically acceptable salts thereof and, in general, they are used as medical or pharmaceutical compositions with carriers or diluents which can be used generally for preparing medicaments. In the case of oral administration, it is most convenient to use the medical compositions of this invention in the form of capsules or tablets but they may be used as sustained release preparations. Furthermore, the compositions may be used as sugar-coated preparations or syrups. The doses thereof at oral administration are 50 to 800 mg per day and it is proper to administer the medicament in 1 to 4 divided doses.

The compounds of this invention of the general formula I are inhibitors for gastric acid secretion having low toxicity which were proved by the following tests.

(i) Gastric acid secretion in anesthetized dogs:

Mongrel dogs weighing 8 to 15 Kg were deprived of food for 24 hrs. and anesthetized intravenously with pentobarbital (30 mg/Kg). A stainless steel cannula was introduced through the ventral wall of the stomach after ligation of the pylorus and esophagus (Okabe, S. et al.: Japan J. Pharmacol. 27, 17-22, 1977). The gastric juice was collected from the gastric cannula by gravity drainage every 15 min. Test compounds were given intravenously after gastric secretion induced by a continuous intravenous infusion of histamine (160 μg/Kg-hr) reached a steady state. The acidity of the gastric juice was measured by titration with 0.05 N NaOH using an automatic titrator (Kyoto Electronics Manufacturing Co., AT-107). The percent inhibition of gastric secretion by each dose of drugs was calculated from the difference between the predrug acid output and the minimum acid output which was usually obtained within 45 min. after drug administration. The dose producing 50% inhibition of the acid output was obtained from the dose-response curve in which the inhibition was semi-logarithmically plotted against dose. The data are shown in Table I, under column entitled (A).

(ii) Gastric acid secretion in pylorus-ligated rats:

Male Wister rats weighing about 200 g were deprived of food for 24 hrs. but allowed free access to water prior to the experiments in individual cages. The pylorus was ligated under ether anesthesia according to the method of Shay et al. (Gastroenterol. 5, 43–61, 1945). Test compounds were intraduodenally given immediately after the ligation of pylorus. The animals were sacrificed 4 hrs. after drug administration and gastric contents were collected. The acidity of gastric juice was measured by titration with 0.05 N NaOH using an automatic titrator (Kyoto Electronics Manufacturing Co., AT-107). The percent inhibition of gastric secretion by each dose of drugs was calculated from the acid outputs of control and of treated groups. $ED_{50}$ values were determined by the probit method. The data are shown in Table I, under column entitled (B).

(iii) Acute toxicity in mice:

Drugs were injected intravenously in male ICR mice weighing about 35 g at a rate of 0.1 ml/10 g/10 sec and the animals were kept under observation for 7 days. $LD_{50}$ values were determined by the up and down method using 10 animals. The data are shown in Table I, under column entitled (C).

TABLE I

| | Pharmacological activities of $H_2$-blockers | | |
|---|---|---|---|
| Compound | (A) Gastric secretion $ED_{50}$ (μg/Kg i.v.) | (B) Pylorus-ligated rats $ED_{50}$ (mg/Kg i.d.) | (C) $LD_{50}$ (mg/Kg i.v.) in mice |
| Compound of this invention | | | |
| Example 9 (base) | 6.4 ± 0.6 | 12.7 (6.0–26.7) | 97.8 |
| Example 3 (base) | 18.3 ± 0.7 | 13.8 (7.2–26.6) | 146.7 |
| Known compound | | | |
| Compound A *1 (base) (Cimetidine) | 333.3 ± 42.0 | 42.6 (21.8–83.3) | 152.5 |
| Compound B *2 (base) | 35.2 ± 2.2 | 49.3 (26.0–93.5) | 94.6 |

*1 chemical name: N—cyano-N'—methyl-N"{-2-[(4-methyl-5-imidazolyl)methylthio]ethyl}guanidine (a typical compound of U.S. Pat. No. 3,950,333, only this compound is commercially sold)
*2 chemical name: 2-guanidino-4-[2-(2-cyanoguanidino)ethylthiomethyl]thiazole (a typical compound of Belgian Patent No. 866,156)

The guanidinothiazole compounds of this invention shown by the general formula I can be produced by the following processes.

Production process 1:

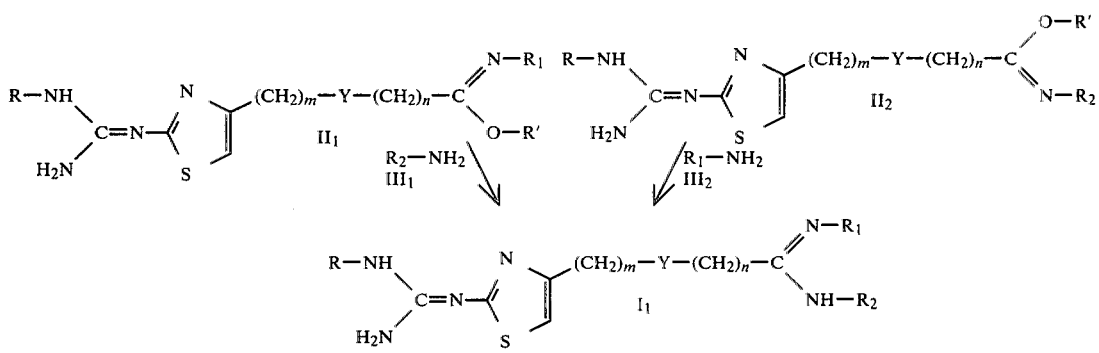

In the above formulae, R' represents a lower alkyl group, and R, $R_1$, $R_2$, Y, m and n have the same significance as above.

This process is performed either by reacting the starting material compound of formula $II_1$ and a reactive amount of the amine of formula $III_1$, or by reacting the starting material compound of formula $II_2$ and a reactive amount of a compound of the formula $III_2$. The amines shown by the formula $III_1$ or $III_2$ used in the processes are those which are capable to produce the desired product I by the reaction with the starting material compound $II_1$ or $II_2$.

Examples of the compounds of formula $III_1$ are ammonia (ammonium chloride); a lower alkylamine such as methylamine, dimethylamine, ethylamine, isopropylamine, etc.; a lower alkenylamine such as allylamine, 2-butenylamine, etc.; a lower alkynylamine such as propargylamine, pentynylamine, etc.; and the like. Examples of the compounds of formula $III_2$ are ammonia (ammonium chloride); cyanamide; urea; hydroxylamine; an o-lower alkylhydroxylamine such as o-methylhydroxylamine, o-butylhydroxylamine, etc.; a lower acylamine such as acetamide, etc.; acylhydrazine such as acetylhydrazine, benzoylhydrazine, etc.; benzenesulfonylhydrazine; semicarbazide; aralkylamine such as benzylamine, phenethylamine, etc.; glycine; and the like.

The reaction is usually performed in a solvent and suitable solvents include, for example, organic solvents such as methanol, ethanol, isopropanol, chloroform, ether, tetrahydrofuran, benzene, etc. It is preferred that these solvents do not contain water. There is no particular restriction about the reaction temperature but the reaction is preferably performed at room temperature or under heating. Also, it is preferred that the reaction system be in a neutral to basic state.

Production process 2:

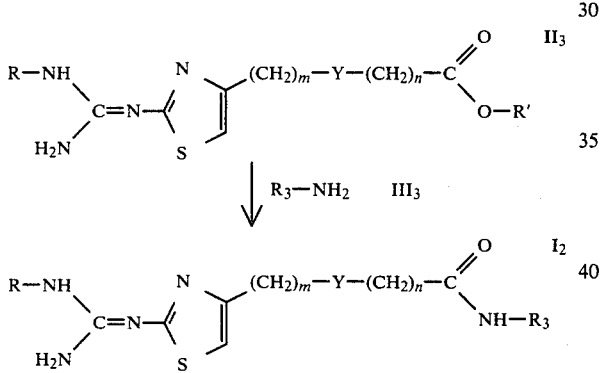

In the above formulae, R, R', $R_3$, Y, m and n have the same significance as above.

This process is performed by reacting the starting material compound of formula $II_3$ and a reactive amount of the amine of formula $III_2$. The starting material compound of formula $II_3$ is obtained by hydrolyzing in a conventional method the starting material compound of formula $II_1$ or $II_2$ wherein $R_1$ or $R_2$ is a hydrogen atom. Examples of the amine shown by formula $III_3$ are ammonia; a lower alkylamine such as methylamine, ethylamine, isopropylamine, etc.; hydroxylamine; and the like. The reaction conditions such as reaction solvent, reaction temperature, etc., are the same as those of the production process 1.

Furthermore, as other processes of producing the desired products of this invention, there are some processes such as a process of converting mutually $R_1$ or $R_2$ of the desired product I, and the like. For example, there are following processes:

(i) The desired product of formula I (where A represents the group shown by

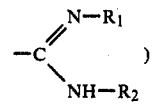

wherein $R_1$ is a carbamoyl group is obtained by passing dry hydrogen chloride gas through an alcohol containing the compound of formula I wherein $R_1$ is a cyano group under cooling or treating the said compound with concentrated hydrochloric acid.

(ii) The desired product of formula I (where A represents the group shown by

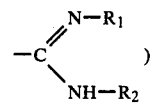

wherein $R_1$ and $R_2$ represent the same lower acyl group, is obtained by reacting a lower acyl halide and the compound of formula I wherein both of $R_1$ and $R_2$ represent a hydrogen atom.

(iii) The desired product of formula I (where A represents the group shown by

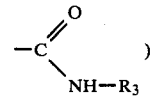

wherein $R_3$ represents —$SO_2NH_2$ is obtained by hydrolyzing the compound of formula I where A represents the group shown by

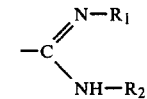

wherein $R_1$ represents a sulfamoyl group and $R_2$ represents a hydrogen atom.

Then, the process of this invention will further be explained by the following examples. In the examples, mp, Anal., NMR and Mass. are abbreviations for melting point, elementary analysis values, nuclear magnetic resonance spectrum and mass spectrum, respectively.

EXAMPLE 1

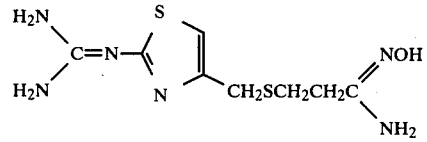

In 35 ml of methanol was dissolved 4.72 g of methyl 3-[(2-guanidinothiazol-4-yl)methylthio]propionimidate and then 25 ml of a methanol solution of free hydroxylamine prepared by treating 1.2 g of hydroxylamine hydrochloride with 0.93 g of sodium methoxide was added to the solution. After stirring the mixture for 2 hours at room temperature, the solvent was distilled off under reduced pressure and the residue formed was purified by a column chromatography using a mixed solvent of chloroform and methanol as a developing solvent and recrystallized from methanol-acetone to provide 1.3 g of 3-[(2-guanidinothiazol-4-yl)methylthio]propionamidoxime. The product has the following physicochemical properties:

(i) Melting point: 177°–179° C. (decompd.)
(ii) Elemental analysis for $C_8H_{14}N_6OS_2\cdot\tfrac{1}{4}H_2O$

|  | C | H | N |
|---|---|---|---|
| Calculated: | 34.46% | 5.24% | 30.14% |
| Found: | 34.78% | 5.23% | 30.06% |

In addition, methyl 3-[(2-guanidinothiazol-4-yl)methylthio]propionimidate used as the raw material in this example was prepared by the following method.

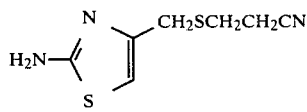

in a mixture of 490 ml of water and 320 ml of ethanol was dissolved 98.1 g of S-(2-aminothiazol-4-ylmethyl)isothiourea 2-hydrochloride (see, "J. Amer. Chem. Soc.", 68, 2155–2159(1946)) in a nitrogen stream and after adding thereto 37.0 g of 3-chloro-propionitrile, the mixture was cooled to 0°–10° C. and a solution of 45.1 g of sodium hydroxide in 450 ml of water was added dropwise to the mixture. Thereafter, the mixture was stirred for one hour at 0°–10° C. and further for one hour at room temperature and the product formed was extracted 4 times each time with 600 ml of chloroform.

The chloroform layer obtained was washed with water and dried with anhydrous magnesium sulfate. Then, the solvent concentrated off under reduced pressure and the crystals deposited were collected by filtration to provide 47.2 g of 3-(2-aminothiazol-4-ylmethylthio)propionitrile showing a melting point of 104°–106° C.

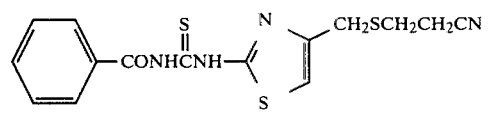

In 500 ml of acetone was dissolved 50 g of 3-(2-aminothiazol-4-ylmethylthio)propionitrile and after adding thereto 45 g of benzoyl isothiocyanate, the mixture was refluxed under heating for 5 hours. Thereafter, the solvent was concentrated off under reduced pressure and the crystals deposited were collected by filtration to provide 79.4 g of the needle crystals of 3-[2-(3-benzoylthioureido)thiazol-4-ylmethylthio]propionitrile showing a melting point of 158°–160° C.

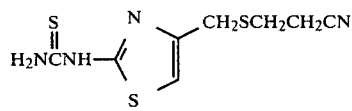

In a mixture of 1400 ml of acetone and 350 ml of methanol was dissolved 80 g of 3-[2-(3-benzoylthioureido)-thiazol-4-ylmethylthio]propionitrile and after adding thereto a solution of 20 g of potassium carbonate in 300 ml of water, the mixture was stirred for 5 hours at 50° C. Then, the solvents were concentrated off under reduced pressure, the residue formed was added to 2,000 ml of ice water followed by stirring for 24 hours, and the crystals deposited were collected by filtration to provide 53.3 g of 3-(2-thioureidothiazol-4-ylmethyltio)propionitrile showing a melting point of 135°–137° C.

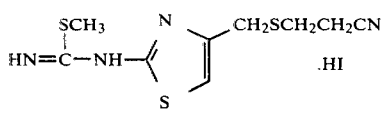

In 200 ml of ethanol was dissolved 15 g of 3-(2-thioureidothiazol-4-ylmethylthio)propionitrile and after adding thereto 12.4 g of iodomethane, the mixture was refluxed under heating for one hour. Then, the solvent was concentrated off under reduced pressure and the crystals deposited were collected by filtration to provide 20.9 g of 3-[2-(S-methylisothioureido)thiazol-4-ylmethylthio]propionitrile hydroiodide having a melting point of 148°–149° C. (decompd.).

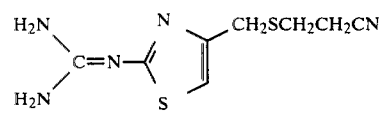

In 200 ml of methanol containing 17.0 g (1.0 mole) of ammonia were dissolved 20 g (0.05 mole) of 3-[2-(S-methylisothioureido)thiazol-4-ylmethylthio]propionitrile hydroiodide and 2.68 g (0.05 mole) of ammonium chloride and the solution was heated in a sealed tube to 80°–90° C. for 15 hours.

After cooling the reaction mixture, the solvent was distilled off under reduced pressure. To the residue obtained was added 200 ml of water and the mixture was alkalified by the addition of a saturated aqueous solution of potassium carbonate. Then, the brown precipitates deposited were collected by filtration, air-dried, and recrystallized from acetone to provide 6.2 g of 3-(2-guanidinothiazol-4-ylmethylthio)propionitrile showing a melting point of 132° C.

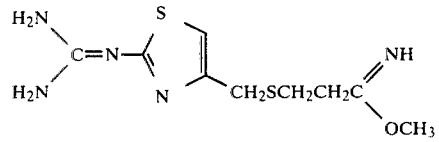

In a mixture of 60 ml of anhydrous methanol and 120 ml of anhydrous chloroform was dissolved 10 g of 3-(2-guanidinothiazol-4-ylmethylthio)propionitrile and after cooling the solution to 0°–10° C. in nitrogen stream and passing therethrough a dry hydrogen chloride gas for 3 hours, the solution was allowed to stand in a closed vessel at 0°–4° C. for 20 hours.

Then, the solvents were distilled off under reduced pressure and the concentrated residue was poured into 200 ml of ice-water containing 30 g of potassium carbonate, and the mixture solution was extracted three times with 150 ml of chloroform containing 20% methyl alcohol.

The organic layer was dried over anhydrous magnesium sulfate, and the solvent was distilled away under reduced pressure to provide 10.3 g of methyl-3-[(2-guanidinothiazol-4-yl)methylthio]propionimidate.

EXAMPLE 2

By following the reaction procedure as in Example 1, the following compound was prepared.

o-Methyl-3-[(2-guanidinothiazol-4-yl)methylthio]-propionamidoxime maleate.

The amine used for the reaction: $H_2NOCH_3$
The physicochemical properties of the product:
(i) Melting point: 161°–164° C.
(ii) Elemental analysis for $C_{14}H_{21}O_6N_6S_2 \cdot \frac{1}{2}H_2O$:

|  | C | H | N |
|---|---|---|---|
| Calculated: | 38.00% | 5.01% | 18.99% |
| Found: | 38.04% | 4.94% | 19.31% |

EXAMPLE 3

To 1.9 g of ethyl 3-[(2-guanidinothiazol-4-yl)methylthio]-propionimidate was added 10 ml of an ethanol solution of 0.28 g of cyanamide and the mixture was allowed to stand overnight at room temperature. Then, the solvent was distilled off from the reaction mixture under reduced pressure and the residue obtained was purified by a silica gel column chromatography using a solvent mixture of chloroform and methanol as a developing solvent to provide 1.35 g of N-cyano-3-[(2-guanidinothiazol-4-yl)methylthio]propionamidine. The product shows the following physicochemical properties:

(i) Melting point: 102.5°–104° C. (recrystallized from methanol-ether).
(ii) Elemental analysis for $C_9H_{13}N_7S_2$:

|  | C | H | N |
|---|---|---|---|
| Calculated: | 38.15% | 4.62% | 34.60% |
| Found: | 37.84% | 4.59% | 34.26% |

EXAMPLES 4–8

By following the reaction procedure as in Example 3, the following compounds were prepared:

EXAMPLE 4

N-(2-Propinyl)-3-[(2-guanidinothiazol-4-yl)methylthio]-propionamidine.

The amine used for the reaction: $H_2NCH_2C\equiv CH$
The physicochemical properties of the product:
(i) Mass spectrum: m/e 296(M+)
(ii) Nuclearmagnetic resonance spectra (DMSO-$d_6$+CD$_3$OD)

δ: 2.30 (2H, t), 2.70 (2H, t) } SCH$_2$CH$_2$), 2.83 (1H, t, CH$_2$C≡CH)

3.60 (2H, S, ⟩—CH$_2$S$^-$), 3.70 (2H, d, NCH$_2$C≡CH), 6.48 (1H, S, thiazole-H)

EXAMPLE 5

N-Benzyl-3-[(2-guanidinothiazol-4-yl)methylthio]-propionamidine.

The amine used for the reaction:

$H_2NCH_2$—C$_6$H$_5$

The physicochemical properties of the product:
(i) Mass spectrum: m/e 241 (M—NH$_2$CH$_2$C$_6$H$_5$)
(ii) Nuclear magnetic resonance spectra (DMSO-$d_6$):

δ: 2.38 (2H, t), 2.75 (2H, t) } SCH$_2$CH$_2$), 3.60 (2H, S, ⟩—CH$_2$S$^-$), 4.17 (2H, S, NCH$_2$—C$_6$H$_5$), 6.45 (1H, S, thiazole-H), 7.30 (5H, S, C$_6$H$_5$).

EXAMPLE 6

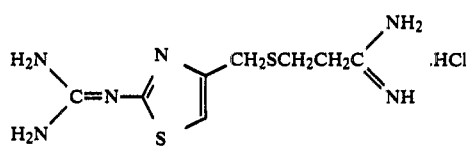

3-[(2-Guanidinothiazol-4-yl)methylthio]propionamidine hydrochloride.

The amine used for the reaction: NH$_4$Cl
The physicochemical properties of the product:
(i) Melting point: 109°–112° C.
(ii) Elemental analysis for C$_8$H$_{15}$N$_6$S$_2$Cl:

|  | C | H | N |
|---|---|---|---|
| Calculated: | 32.59% | 5.13% | 28.51% |
| Found: | 32.33% | 5.01% | 28.28% |

EXAMPLE 7

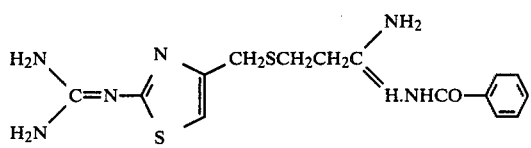

N-Benzoyl-3-[(2-guanidinothiazol-4-yl)methylthio]-propionamidrazone.

The amine used for the reaction:

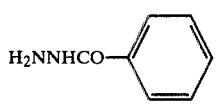

The physicochemical properties of the product:
(i) Melting point: 103°–106° C.
(ii) Elemental analysis for C$_{15}$H$_{19}$N$_7$OS$_2$:

|  | C | H | N |
|---|---|---|---|
| Calculated: | 47.73% | 5.01% | 25.97% |
| Found: | 47.43% | 5.00% | 25.72% |

EXAMPLE 8

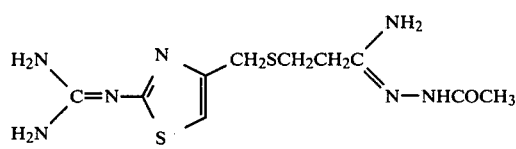

N-Acetyl-3-[(2-guanidinothiazol-4-yl)methylthio]-propionamidrazone.

The amine used for the reaction: H$_2$NNHCOCH$_3$
The physicochemical properties of the product:
(i) Melting point: 163°–166° C.
(ii) Elemental analysis for C$_{10}$H$_{17}$N$_7$OS$_2$:

|  | C | H | N |
|---|---|---|---|
| Calculated: | 38.08% | 5.43% | 31.09% |
| Found: | 37.86% | 5.62% | 30.73% |

EXAMPLE 9

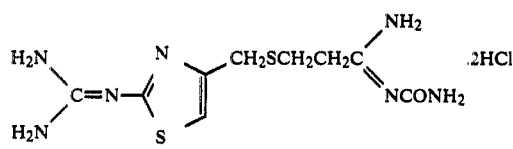

In a mixture of 15 ml of ethanol and 10 ml of chloroform was dissolved 0.5 g of N-cyano-3-[(2-guanidinothiazol-4-yl)-methylthio]propionamidine and after passing through the solution a dry hydrogen chloride gas for 1.5 hours under cooling by ice water, the reaction mixture was concentrated under reduced pressure. To the residue was added 10 ml of ethanol, the mixture was concentrated again under reduced pressure. The residue formed was dissolved in a small amount of ethanol and after adding thereto ether and allowing to stand overnight the mixture, the crystals deposited were collected by filtration to provide 0.55 g of N-carbamoyl-3-[(2-guanidinothiazol-4-yl)methylthio]propionamidine.dihydrochloride. The product shows the following physicochemical properties:
(i) Melting point: 171°–173° C.
(ii) Elemental analysis for C$_9$H$_{17}$N$_7$S$_2$OCl$_2$:

|  | C | H | N |
|---|---|---|---|
| Calculated: | 28.88% | 4.58% | 26.19% |
| Found: | 28.73% | 4.64% | 25.78% |

EXAMPLE 10

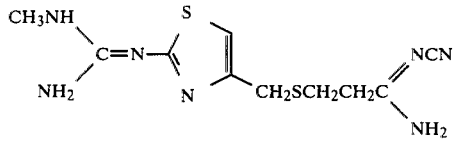

In 30 ml of ethanol was dissolved 6.4 g of methyl 3-(2-methylguanidinothiazol-4-ylmethylthio)propionimidate and after adding thereto 0.9 g of cyanamide and stirring the mixture for 2 hours at room temperature, the solvent was distilled off under reduced pressure. Then, the residue obtained was purified by column chromatography using a mixture of chloroform and methanol as the developing solvent and recrystallized from ethanol to provide 2.0 g of N-cyano-3-(2-methylguanidinothiazol-4-ylmethylthio)propionamidine showing a melting point of 144°–145° C.

Elemental analysis for C$_{10}$H$_{15}$N$_7$S$_2$:

|  | C | H | N |
|---|---|---|---|
| Calculated: | 40.39% | 5.08% | 32.97% |
| Found: | 40.13% | 5.00% | 32.68% |

EXAMPLE 11

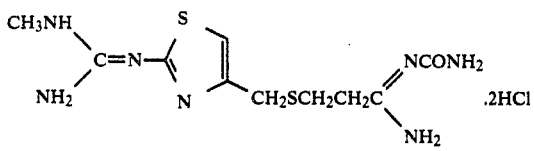

In a mixture of 20 ml of ethanol, 30 ml of chloroform, and 10 ml of methanol was dissolved 1.0 g of N-cyano-3-(2-methylguanidinothiazol-4-ylmethylthio)propionamidine and after cooling the solution to 0°-5° C. and passing therethrough a hydrogen chloride gas for one hour, the solvents were distilled off under reduced pressure. Then, the residue formed was recrystallized from ethanol to provide 1.2 g of N-carbamoyl-3-(2-methylguanidinothiazol-4-ylmethylthio)-propionamidine.di-hydrochloride showing a melting point of 180°-182° C.

Elemental analysis for $C_{10}H_{19}N_7OS_2Cl_2 \cdot \frac{1}{2}H_2O$:

|  | C | H | N |
|---|---|---|---|
| Calculated: | 30.23% | 5.07% | 24.68% |
| Found: | 30.52% | 5.06% | 24.41% |

EXAMPLE 12

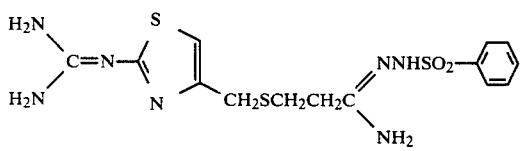

In 49 ml of methanol were dissolved 2.0 g of methyl 3-(2-guanidinothiazol-4-ylmethylthio)propionimidate and 1.21 g of benzenesulfonylhydrazine and after stirring the solution for 24 hours at room temperature, the solvent was distilled off under reduced pressure. Then, the residue formed was purified by a column chromatography using a mixture of chloroform and methanol as the developing solvent to provide 1.2 g of N-benzenesulfonyl-3-(2-guanidinothiazol-4-ylmethylthio)propionamidrazone showing a melting point of 159.5°-161° C.

Elemental analysis for $C_{14}H_{19}N_7O_2S_3$:

|  | C | H | N |
|---|---|---|---|
| Calculated: | 40.66% | 4.63% | 23.71% |
| Found: | 40.30% | 4.54% | 23.46% |

EXAMPLE 13

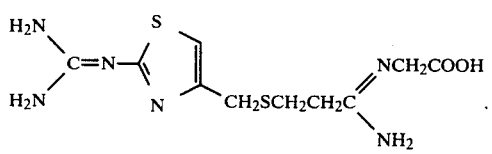

In 20 ml of methanol was suspended 2 g of methyl 3-(2-guanidinothiazol-4-ylmethylthio)propionimidate and then a solution of 0.5 g of glycine in 5 ml of water was added to the suspension. After stirring the mixture for 2 hours at room temperature, the solvent was distilled off under reduced pressure and the residue formed was recrystallized from a mixture of water and acetone to provide 1.0 g of 3-(2-guanidinothiazol-4-ylmethylthio)propionamidinoglycine showing a melting point of 140°-141° C. (decompd.).

Elemental analysis for $C_{10}H_{16}N_6O_2S_2 \cdot 2\frac{1}{4}H_2O$:

|  | C | H | N |
|---|---|---|---|
| Calculated: | 33.65% | 5.79% | 23.55% |
| Found: | 33.82% | 5.43% | 23.65% |

EXAMPLE 14

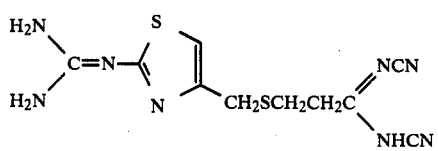

In 35 ml of methanol was dissolved 5.1 g of methyl 3-(2-guanidinothiazol-4-methylthio)propionimidate and after adding 0.9 g of cyanamide to the solution and stirring the mixture for 24 hours at room temperature, the solvent was distilled off under reduced pressure. Then, the residue formed was purified by a column chromatography using a mixture of chloroform and methanol as the developing solvent to provide 4.8 g of N-cyano-3-(2-guanidinothiazol-4-ylmethylthio)-propionamidine and 0.3 g of N,N'-dicyano-3-(2-guanidinothiazol-4-yl)methylthiopropionamidine showing a melting point of 223°-224° C. (decompd.).

Mass. (FD method); m/e 309 (M$^+$ + 1)
NMR (d$_6$DMSO): δ  2.5-2.8 (4H, m, —SCH$_2$CH$_2$—),
3.75 (2H, s, —CH$_2$S—)

7.10 (1H, s, 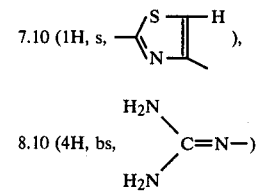 ), 8.10 (4H, bs, $\begin{array}{c}H_2N\\ \diagdown\\ C=N-\\ \diagup\\ H_2N\end{array}$ )

EXAMPLE 15

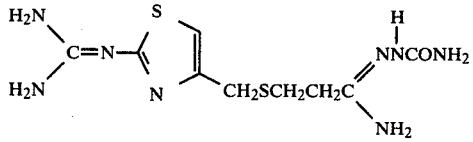

To a solution of 246.6 mg of potassium tertiary butoxide in 10 ml of anhydrous methanol was added 245.3 mg of semicarbazide hydrochloride under ice cooling and after stirring the mixture for 10 minutes at room temperature, a solution of 540 mg of methyl 3-[(2-guanidinothiazol-4-yl)thiomethyl]-propionimidate was added to the mixture. After stirring the mixture for 2 days at room temperature, the solvent was distilled off under reduced pressure and the residue formed was purified by a silica gel column chromatography using a mixture of chloroform and methanol to provide 0.4 g of N-carbamoylamino-3-(2-guanidinothiazol-4-yl)methylthio]-propionamidine. The product was dissolved in 5 ml of methanol and after adding 0.4 g of maleic acid to the solution and stirring the mixture for 10 minutes, the solvent was distilled off, 20 ml of acetone was added to the residue, and insoluble matters were filtered off to provide 0.3 g of N-carbamoylamino-3-[(2-guanidinothiazol-4-yl)-methylthio]propionamidine.dimaleate mono-hydrate showing a melting point of 109°–111° C.

Elemental analysis for $C_{17}H_{26}N_8S_2O$:

|  | C | H | N | S |
| --- | --- | --- | --- | --- |
| Calculated: | 36.04% | 4.59% | 19.79% | 11.30% |
| Found: | 36.01% | 4.53% | 19.55% | 11.37% |

EXAMPLE 16

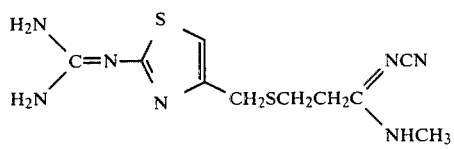

To 5.2 g of methyl N-cyano-3-[(2-guanidinothiazol-4-yl)-methylthio]propionimidate was added 50 ml of a methanol solution of 40% methylamine and after allowing to stand the mixture for 20 hours at room temperature, the solvent was distilled off under reduced pressure. The residue formed was purified by a column chromatography using a mixture of chloroform and methanol as the developing solvent, the product thus purified was converted into the maleate in acetone and recrystallized from methanol to provide 1.0 g of N-cyano-N'-3-(2-guanidinothiazol-4-ylmethylthio)propionamidine showing a melting point of 159°–161° C.

Elemental analysis for $C_{16}H_{21}N_7O_6S_2 \cdot \frac{1}{2}H_2O$:

|  | C | H | N |
| --- | --- | --- | --- |
| Calculated: | 39.99% | 4.61% | 20.40% |
| Found: | 39.89% | 4.69% | 20.24% |

In addition, methyl {N-cyano-3-[(2-guanidinothiazol-4-yl)-methylthio]} propionimidate used in the example as the raw material is obtained by the following method.

In a mixture of 90 ml of dessicated chloroform and 40 ml of dessicated methanol was dissolved 7.5 g of 3-(2-guanidinothiazol-4-ylmethylthio)propionitrile and after cooling the solution to 0°–10° C. in nitrogen stream and passing therethrough 25 g of a hydrogen chloride gas, the solution was allowed to stand for 48 hours at 0°–10° C. Then, the solvent was distilled off under reduced pressure and the residue formed was dissolved in 50 ml of dessicated methanol and after adding thereto 1.3 g of cyanamide, the mixture was stirred for 3.5 hours at room temperature. Thereafter, the solvent was concentrated off under reduced pressure and after adding 50 ml of ice water having dissolved therein 12 g of potassium carbonate to the residue formed, the product was extracted three times each time with 50 ml of chloroform. The extract obtained was dried by anhydrous magnesium sulfate and then the solvent was distilled off under reduced pressure.

EXAMPLE 17

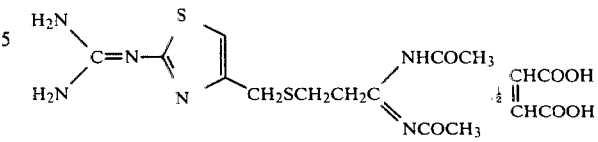

In 10 ml of dimethylformamide was dissolved 1.2 g of 3-[2-guanidinothiazol-4-ylmethylthio]propionamidine and after adding 0.4 g of triethylamine to the solution and cooling the mixture below 15° C., a solution of 1.4 g of acetyl chloride in 3 ml of chloroform was added dropwise to the mixture. Thereafter, the mixture was stirred for 30 minutes at room temperature and then the solvent was distilled off. To the residue formed was added a solution of 0.8 g of potassium carbonate in 2 ml of water. After distilling off water, the residue was subjected to a silica gel column chromatography and the product was developed by a mixture of chloroform and methanol. Then, the eluant was distilled off to provide 0.3 g of N,N'-diacetyl-3-(2-guanidinothiazol-4-ylmethylthio)propionamidine. The product was added to a solution of 0.2 g of maleic acid in 10 ml of acetone followed by stirring for 30 minutes at room temperature. The precipitates formed were collected by filtration to provide 0.2 g of N,N'-diacetyl-3-(2-guanidinothiazol-4-ylmethylthio)-propionamidine.$\frac{1}{2}$maleate.$H_2O$ showing a melting point of 180°–181° C.

Elemental analysis for $C_{14}H_{22}N_6S_2O_5$:

|  | C | H | N | S |
| --- | --- | --- | --- | --- |
| Calculated: | 40.19% | 4.52% | 20.00% | 15.30% |
| Found: | 39.91% | 4.53% | 20.01% | 15.27% |

EXAMPLE 18

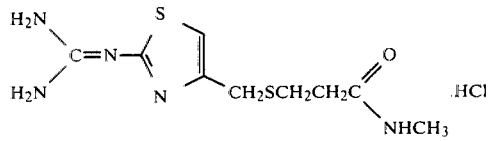

In 30 ml of a methanol solution of 40% methylamine was dissolved 3 g of methyl 3-(2-guanidinothiazol-4-ylmethylthio)propionate and after allowing to stand the solution for 24 hours at room temperature, the solvent was distilled off under reduced pressure. The residue formed was purified by a column chromatography using a mixture of chloroform and methanol as the developing solvent, the product thus purified was converted into the hydrochloride by treatment with hydrochloric acid and recrystallized from a mixture of isoproanol and ethyl acetate to provide 1.5 g of N-methyl-3-(2-guanidinothiazol-4-ylmethylthio)propionamide hydrochloride showing a melting point of 126°–127° C.

Elemental analysis for $C_9H_{16}N_5OS_2Cl$

|  | C (%) | H (%) | N (%) |
| --- | --- | --- | --- |
| Calculated: | 34.89 | 5.20 | 22.60 |
| Found: | 34.51 | 5.19 | 22.55 |

In addition, methyl 3-(2-guanidinothiazol-4-ylmethylthio)propionate used in the example as the starting material was prepared by the following method.

In a mixture of 60 ml of methanol and 120 ml of chloroform was dissolved 10 g of 3-(2-guanidinothiazol-4-ylmethylthio)propionitrile and after cooling the solution to 0°–10° C. and passing therethrough 30 g of a hydrogen chloride gas, the solution was allowed to stand for 20 hours at 0°–10° C. To the reaction mixture was added 0.7 ml of water and after allowing to stand the mixture for 20 hours at room temperature, the reaction mixture was added to 250 ml of ice water containing 120 g of potassium carbonate and extracted 4 times each time with 100 ml of chloroform containing 20% methanol. The extract obtained was concentrated under reduced pressure and the residue was purified by a column chromatography using a mixture of chloroform and methanol as the developing solvent to provide 5.0 g of methyl 3-(2-guanidinithiazol-4-ylmethylthio)propionate showing a melting point of 106°–107° C.

EXAMPLE 19

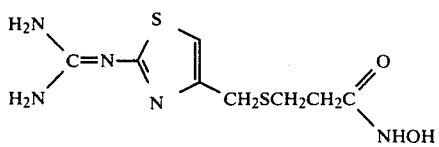

By following the same procedure as in Example 18 using, however, hydroxylamine in place of methylamine, 3-(2-guanidinothiazol-4-ylmethylthio)propionhydroxamic acid was obtained.

The product has the following physicochemical properties:

(i) Melting point: 155°–156° C.
(ii) NMR (DMSO-d$_6$)

δ: 2.24 (2H, t, —CH$_2$—C$\overset{\displaystyle O}{\diagdown}$ )

2.66 (2H, t, —SCH$_2$CH$_2$—)
3.58 (2H, s, —CH$_2$S—)

6.48 (1H, s, —⟨S⟩—H)

(iii) Mass.(FD method) m/e 276 (M$^+$+1)

EXAMPLE 20

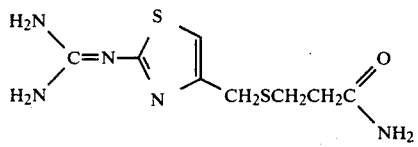

In a mixture of 30 ml of ethanol and 30 ml of water was dissolved 5.0 g of methyl 3-(2-guanidinothiazol-4-ylmethylthio)propionimidate and after allowing to stand the solution for 20 hours at 40° C., the solvent was distilled off under reduced pressure. The residue formed was purified by a column chromatography using a mixture of chloroform and methanol and recrystallized from methanol to provide 3.2 g 3-(2-guanidinothiazol-4-ylmethylthio)propionamide showing a melting point of 193°–194° C. (decompd.).

Elemental analysis for C$_8$H$_{13}$N$_5$OS$_2$:

|  | C | H | N |
|---|---|---|---|
| Calculated: | 37.05% | 5.05% | 27.00% |
| Found: | 36.97% | 5.06% | 26.84% |

EXAMPLE 21

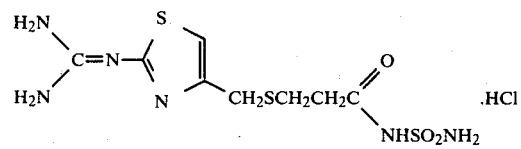

In 50 ml of 1 N HCl was dissolved 2.5 g of N-sulfamoyl-3-(2-guanidinothiazol-4-ylmethylthio)propionamidine and after stirring the solution for 2 hours at 40° C., the crystals deposited were collected by filtration and recrystallized from a mixture of methanol and ethyl acetate to provide 1.65 g of 3-(2-guanidinothiazol-4-ylmethylthio)propionylsulfamide hydrochloride showing a melting point of 166°–167° C.

Elemental analysis for C$_8$H$_{15}$N$_6$O$_3$S$_3$Cl.H$_2$O:

|  | C | H | N |
|---|---|---|---|
| Calculated: | 24.46% | 4.36% | 21.39% |
| Found: | 24.78% | 4.23% | 21.61% |

EXAMPLE 22

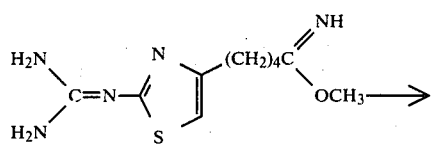

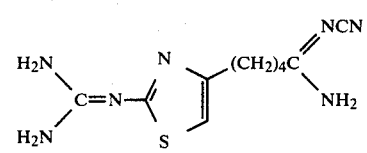

In 10 ml of methanol solution of 2.5 g of methyl 5-(2-guanidinothiazol-4-yl)pentanoimidate was added 0.6 g cyanamide, and the solution was stirred at room temperature for 1.5 hour. The solvent was distilled off, and to the residue was added 10 ml of acetone. The precipitated crystals were filtered off and the product was purified by using dimethylformamide-water. The purified product was dissolved in a mixture of 0.7 ml of acetic acid, 8 ml of ethanol and 16 ml of water, to the solution 11.6 ml of N-NaOH solution was added. The precipitated crystals were collected by filtration to provide 1.9 g of N-cyano-5-(2-guanidinothiazol-4-yl)pentanoamidine.

(i) Melting point: 195°–196° C.
(ii) Elemental analysis for C$_{10}$H$_{15}$N$_7$S

|  | C | H | N |
|---|---|---|---|
| Calculated: | 45.27 | 5.70 | 36.95 |
| Found: | 45.13 | 5.82 | 36.62 |

In addition, methyl 5-(2-guanidinothiazol-4-yl)pentanoimidate used as the starting material in this example was prepared by the following method.

(a) Cl(CH$_2$)$_4$COCl→Cl(CH$_2$)$_4$COCH$_2$CL

In 300 ml of ehter solution of diazomethane prepared from 43 g of p-tosyl-N-methyl-N-nitrosoacetamide was added under stirring 30 ml of ether solution of 8 g of 5-chlorovalerylchloride dropwise at −5° to 0° C., and the solution was allowed to stand at the same temperature for 2 hours. Hydrogen chloride gas was passed through the reaction solution at 0° C. and the solution was allowed to stand at the same temperature for 0.5 hours. To the solution was added 100 ml of water and the ether layer was separated. The aqueous layer was further extracted twice each time with 100 ml of ether. The ether layers were combined and the obtained ether solution was dried over anhydrous magnesium sulfate and the solvent was distilled away and the residue was distilled under reduced pressure to provide 8.2 g of 1,6-dichloro-2-hexanone showing a boiling point of 120° to 125° C. (14 mm Hg).

ClCH$_2$CO(CH$_2$)$_4$Cl ⟶ (b)

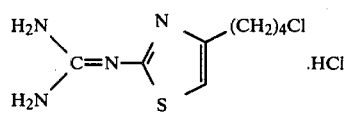

In 200 ml of acetone solution of 23.5 g of 1,6-dichloro-2-hexanone was added 16.4 g of guanylthiourea and the solution was stirred for two days. The solvent distilled away and the residue was purified by a silica gel column chromatography using a mixture of chloroform and methanol as the developing solvent to provide 2-guanidino-4-(4-chlorobutyl)thiazol hydrochloride (this product shows a melting point of 113° to 114° C. after the recrystallization from a mixture of ethanol and ether). This hydrochloride was dissolved in 300 ml of water, and to the solution was added 100 ml aqueous solution of 17.4 g of potassium carbonate. The obtained solution was extracted three times each time with 500 ml, 200 ml and 200 ml of chloroform. The extracted solution was combined and dried over anhydrous potassium carbonate and the solvent was distilled away. The obtained crystals were recrystallized from a mixture of ether and n-hexane to provide 20 g of 2-guanidino-4-(4-chlorobutyl)thiazole having a melting point of 83° to 84° C.

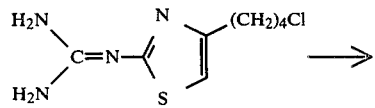 (c)

-continued

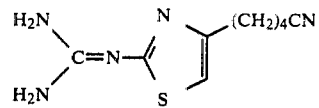

In 24 ml of dimethylsulfoxide was added 4.9 g of sodium cyanide, and the obtained mixture was heated at 70° C. Under stirring, 19.5 g of 2-guanidino-4-(4-chlorobutyl)thiazole was added to the solution at 70° to 75° C., and the solution was stirred at the same temperature for 3 hours. The reaction solution was cooled, and 100 ml of chloroform was added to the solution. After filtering off the undissolved material, the residue was purified by a silica gel column chromatography using a mixture of chloroform and methanol as the developing solvent to provide 15 g of 2-guanidino-4-(4-cyanobutyl)thiazole. The product shows a melting point of 104°–105° C. after recrystallization from a mixture of ethyl acetate and n-hexane.

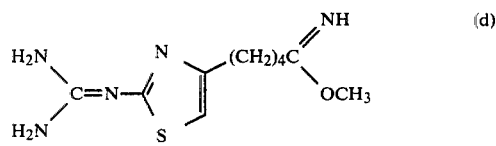 (d)

10 g of 2-guanidino-4-(4-cyanobutyl)thiazole was suspended in a mixture of 60 ml of methanol and 110 ml of chloroform, and hydrogen chloride gas was passed through the solution under stirring at −5° to 5° C. for 2 hours. The resulting solution was allowed to stand at 5° C. for 2 days and the solvent was distilled off. The residue was suspended in a mixture of chloroform and methanol, and the suspension was poured into ice water containing 60 g of potassium carbonate. The chloroform layer was separated, and the aqueous layer was extracted further three times each time with 150 ml of chloroform. The extracts were combined, and dried over anhydrous potassium carbonate. The solvent was distilled off to provide 11 g of methyl 5-(2-guanidinothiazol-4-yl)pentanoimidate having a melting point of 143°–145° C.

EXAMPLE 23

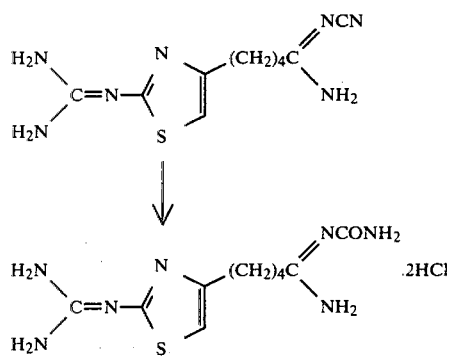

1 g of N-cyano-5-(2-guanidinothiazol-4-yl)pentanoamidine was suspended in a mixture of 20 ml of methanol and 30 ml of chloroform. Hydrogen chloride gas was passed through the suspension for 1.5 hour at −5° to 5° C. and the reaction solution was concentrated under reduced pressure. The oily residue was recrystallized from a mixture of methanol and ether containing a small amount of water to provide 1.1 g of N-carbamoyl-5-(2-guanidinothiazol-4-yl)pentanoamidine dihydrochloride monohydrate having a melting point of 148°–150° C.

Elemental analysis for $C_{10}H_{17}N_7OS \cdot 2HCl \cdot H_2O$

|  | C | H | N |
|---|---|---|---|
| Calculated | 32.09 | 5.65 | 26.20 |
| Found | 32.10 | 5.65 | 26.06 |

EXAMPLE 24

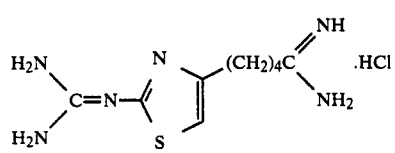

In 5 ml of methanol solution of 0.64 g of methyl 5-(2-guanidinothiazol-4-yl)pentanoimidate was added 0.084 g of ammonium chloride, and the solution was stirred at room temperature overnight. To the reaction solution was added 5 ml of acetone and the precipitated crystals were collected by filtration. The obtained crystals were recrystallized from aqueous ethanol to provide 0.37 g of 5-(2-guanidinothiazol-4-yl)pentanoamidine hydrochloride.

Elemental analysis for $C_9H_{16}N_6S \cdot HCl$

|  | C | H | N |
|---|---|---|---|
| Calculated | 39.06 | 6.19 | 30.36 |
| Found | 39.16 | 6.30 | 30.17 |

EXAMPLE 25

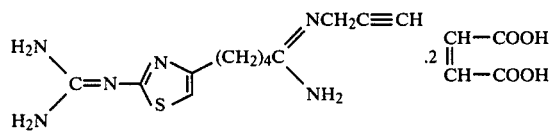

In 5 ml of methanol was dissolved 0.64 g of methyl 5-(2-guanidinothiazol-4-yl)pentanoimidate, and 0.09 g of propargyl amine was added to the solution followed by allowing to stand overnight at room temperature. The solvent was distilled away, and the residue was purified by a silica gel column chromatography using chloroform-methanol-triethylamine as a developing solvent. The obtained oily product was dissolved in acetone, and to the solution acetone solution of 0.4 g of maleic acid was added. The precipitated crystals were collected by filtration, and recrystallized from ethanol to provide 0.14 g of N-propargyl-5-(2-guanidinothiazol-4-yl)pentanoamidine dimaleate.

Elemental analysis for $C_{20}H_{26}N_6O_8S$

|  | C | H | N |
|---|---|---|---|
| Calcd. | 47.05 | 5.13 | 16.46 |
| Found | 46.75 | 5.20 | 16.34 |

By following the reaction procedure as the above Example (the reactant:

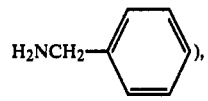

N-benzyl-5-(2-guanidinothiazol-4-yl)pentanoamidine di-maleate having a melting point of 92°–94° C. was obtained.

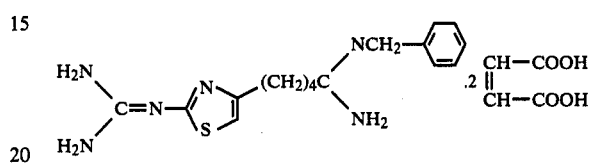

Elemental analysis for $C_{24}H_{30}N_6O_8S$

|  | C | H | N |
|---|---|---|---|
| Calcd. | 51.24 | 5.37 | 14.94 |
| Found | 50.76 | 5.35 | 14.82 |

EXAMPLE 26

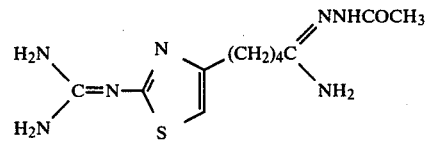

In 5 ml of methanol was dissolved 0.064 g of methyl 5-(2-guanidinothiazol-4-yl)pentanoimidate, and 0.27 g of acetyl hydrazine was added to the solution. The reaction solution was stirred at room temperature overnight, and the precipitated crystals was collected by filtration. The obtained product was washed with ethanol-ether to provide 0.27 g of N-acetyl-5-(2-guanidinothiazol-4-yl)pentanoamidrazone having a melting point of 157°–159° C.

Elemental analysis for $C_{11}H_{19}N_7OS$

|  | C | H | N |
|---|---|---|---|
| Calcd. | 44.43 | 6.44 | 32.97 |
| Found | 44.06 | 6.37 | 32.60 |

By following the reaction procedure as the above Example (the reactant:

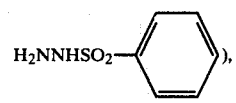

N-benzenesulfonyl-5-(2-guanidinothiazol-4-yl)pentanoamidrazone having a melting point of 206°–207° C. was obtained.

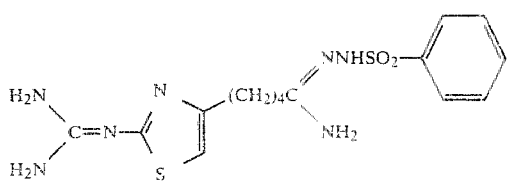

Elemental analysis for $C_{15}H_{21}N_7O_2S_2$

|  | C | H | N |
|---|---|---|---|
| Calcd. | 45.55 | 5.35 | 24.79 |
| Found | 45.33 | 5.38 | 24.79 |

EXAMPLE 27

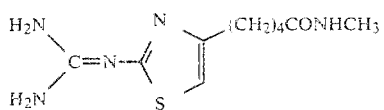

To 0.27 g of 5-(2-guanidinothiazol-4-yl)propionic acid ethyl ester was added 1 ml of 40% methanol solution of methyl amine, and the solution was allowed to stand at room temperature for 2 days. The precipitated crystals were collected by filtration, and washed with methanol and then ether to provide 0.21 g of N-methyl 5-(2-guanidinothiazol-4-yl)pentanoic acid amide. This product was recrystallized from aqueous methanol to provide the purified product having a melting point of 228°-232° C.

Elemental analysis for $C_{10}H_{17}N_5OS$

|  | C | H | N |
|---|---|---|---|
| Calcd. | 47.04 | 6.71 | 27.43 |
| Found | 46.86 | 6.54 | 27.68 |

In addition, 5-(2-guanidinothiazol-4-yl)pentanoic acid ethyl ester used as the starting material in this example was prepared by the following method.

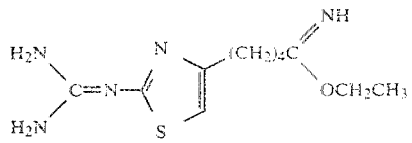

2 g of 2-guanidino-4-(4-cyanobutyl)thiazole was suspended in a mixture of 15 ml of ethanol and 25 ml of chloroform, and hydrogen chloride gas was passed through the solution under stirring at −5° to 5° C. for 2 hours. The resulting solution was allowed to stand at 5° C. for 4 days and the solvent was distilled away under reduced pressure. The residue was suspended in ethanol, and the suspension was poured into ice water containing 15 g of potasium carbonate. The precipitated crystals were collected by filtration washed with water and ether to provide 2.1 g of ethyl 5-(2-guanidinothiazol-4-yl)pentanoimidate having a melting point of 138°-139° C.

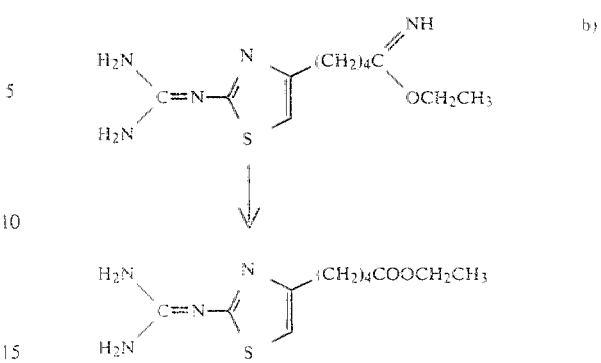

To 1.2 g of ethyl 5-(2-guanidinothiazol-4-yl)pentanoimidate was added 30 ml of ethanol and 3 ml of water. The resulting solution was acidified strongly with ethanolic hydrochloric acid, and was warmed at 50° C. for 10 minutes. After cooling, 30 ml of chloroform and 30 ml of water were added into the reaction solution. The solution was alkalified with potassium carbonate, and the chloroform layer was separated. The aqueous layer was extracted further twice each time with 20 ml of chloroform. The chloroform layers were combined, and dried over anhydrous magnesium sulfate. The solvent was distilled off under reduced pressure, and the residue was purified by a column chromatography using chloroform-methanol as a developing solvent to provide 2.0 g of 5-(2-guanidinothiazol-4-yl)pentanoic acid ethyl ester. This product was recrystallized from ethanol to provide the purified product having a melting point of 109°-110° C.

EXAMPLE 28

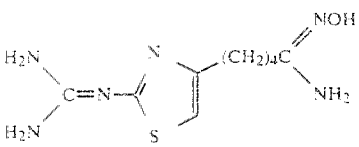

0.13 g of hydroxylamine hydrochloride and 0.117 g of sodium hydroxide were dissolved in 5 ml of methyl alcohol. After adding 0.64 g of methyl 5-(2-guanidinothiazol-4-yl)pentanoimidate, the reaction mixture was allowed to stand at room temperature for three days. The solvent of the reaction mixture was distilled off, and the residue was crystallized by the addition of ethyl alcohol and water. The obtained crystals were dissolved in 0.4 ml of acetic acid, 4 ml of ethyl alcohol and 8 ml of water, and was treated with activated charcoal. To the filtrate was added 6.6 ml of 1 N sodium hydroxide, and the precipitated crystals were collected by filtration to provide 0.24 g of 5-(2-guanidinothiazol-4-yl)pentanoamidoxime having a melting point of 167°-168° C.

Elemental analysis for $C_9H_{16}N_6OS$

|  | C | H | N |
|---|---|---|---|
| Calculated | 42.17 | 6.29 | 32.79 |
| Found | 42.24 | 6.39 | 32.47 |

EXAMPLE 29

Medical composition—tablet for oral administration. Composition for 1,000 tablets:

| Active component | 260 g |
|---|---|
| Starch | 37 g |
| Milk sugar | 50 g |
| Magnesium stearate | 3 g. |

The components shown above were granulated by an ordinary manner using starch paste as a binder and then molded into tables each having 9.5 mm diameter.

EXAMPLE 30

Medical composition—formulation for injection. Composition for 2 ml of injection:

| Active component | 260 mg |
|---|---|
| Distilled water for injection to make | 2 ml. |

Distilled water for injection was added to the active component and the active component was dissolved while passing therethrough a nitrogen gas to provide a solution having a concentration of 13% (a concentration of 10% as a base). After filtering the solution by a bacterial filter, 2.2 ml each of the solution was poured in a 2 milliliter ampule under sterile state and after replacing the space in the ampule with nitrogen gas, the ampoule was sealed.

What is claimed is:

1. A guanidinothiazole compound of the formula $$\begin{array}{c} R-NH \\ \phantom{R-N}\diagdown \\ \phantom{R-NH}C=N \\ \phantom{R-}\diagup \\ H_2N \end{array} \underset{S}{\overset{N}{\diagdown\hspace{-4pt}\diagup}} -(CH_2)_m-Y-(CH_2)_n-A$$

wherein R represents a hydrogen atom or a lower alkyl group, Y represents a sulfur atom or a methylene group, m and n each represent an integer of 1–3, A represents the group $$-C\overset{\displaystyle N-R_1}{\underset{\displaystyle NH-R_2}{\diagdown}} \quad \text{or} \quad -CONH-R_3$$

wherein $R_1$ represents a member selected from the group consisting of a hydrogen atom, a cyano group, a carbamoyl group, a ureido group, a hydroxyl group, a lower alkoxy group, a lower alkylcarbonyl group of a straight or branched carbon chain having 1–5 carbon atoms, a lower alkylcarbonylamino group of straight or branched carbon chain having 1–5 carbon atoms, a benzoylamino group, a naphthoylamino group, a —NH—SO$_2$-phenyl group, a —NH—SO$_2$-naphthyl group, a benzyl group, a phenethyl group, and a carboxymethyl group, $R_2$ represents a member selected from the group consisting of a hydrogen atom, a lower alkyl group, a lower alkenyl group, a lower alkynyl group, a cyano group, and a lower alkylcarbonyl group of a straight or branched carbon chain having 1–5 carbon atoms, and $R_3$ represents a member selected from the group consisting of a hydrogen atom, a lower alkyl group, a hydroxyl group, and a sulfamoyl group, and the pharmacologically acceptable acid addition salts thereof.

2. A compound as claimed in claim 1 wherein said R represents a hydrogen atom, Y represents a sulfur atom, and A represents the group shown by $$-C\overset{\displaystyle N-R_1}{\underset{\displaystyle NH-R_2}{\diagdown}}$$

wherein $R_1$ and $R_2$ have the same significance as above.

3. A compound as claimed in claim 1 wherein said $R_2$ represents a member selected from the group consisting of a hydrogen atom, a lower alkyl group, a cyano group, and a lower alkylcarbonyl group of a straight or branched carbon chain having 1–5 carbon atoms.

4. A compound as claimed in claim 1 which is N-cyano-3-[(2-guanidinothiazol-4-yl)methylthio]propionamidine.

5. A compound as claimed in claim 1 which is N-carbamoyl-3-[(2-guanidinothiazol-4-yl)methylthio]propionamidine.

6. A pharmaceutical composition comprising a gastric acid secretion inhibiting amount of a compound of claim 1 in combination with a pharmaceutically acceptable carrier or diluent.

7. A composition according to claim 6 wherein the guanidinothiazole compound is N-cyano-3-[(2-guanidinothiazol-4-yl)methylthio]propionamidine.

8. A composition according to claim 6 wherein the guanidinothiazole compound is N-carbamoyl-3-[(2-guanidinothiazol-4-yl)methylthio]propionamidine.

9. A pharmaceutical composition comprising a histamine H$_2$-receptor blocking amount of a compound of claim 1 in combination with a pharmaceutically acceptable carrier or diluent.

* * * * *